United States Patent [19]
Whiteside et al.

[11] Patent Number: 5,501,688
[45] Date of Patent: Mar. 26, 1996

[54] SURGICAL DEVICE FOR MANIPULATING WIRE

[75] Inventors: Leo A. Whiteside, Chesterfield; Stephen E. White, Ballwin, both of Mo.

[73] Assignee: Surgical Accessories, Inc., Bridgeton, Mo.

[21] Appl. No.: 198,105

[22] Filed: Feb. 17, 1994

[51] Int. Cl.$^6$ .......................... A61B 17/88; A61B 17/56
[52] U.S. Cl. ......................... 606/103; 606/148; 140/119
[58] Field of Search ........................ 606/86, 103, 148; D8/59; 140/118, 119

[56] References Cited

U.S. PATENT DOCUMENTS

| | | | |
|---|---|---|---|
| 1,120,575 | 12/1914 | Wertz | 140/118 |
| 1,365,649 | 1/1921 | Bates | 140/119 |
| 4,587,963 | 5/1986 | Leibinger et al. | |

FOREIGN PATENT DOCUMENTS

| | | | |
|---|---|---|---|
| 548197 | 10/1957 | Canada. | |
| 595368 | 7/1959 | Italy | 140/118 |
| 84107 | 10/1918 | Switzerland | 140/118 |
| 2207055 | 1/1989 | United Kingdom. | |

OTHER PUBLICATIONS

Zimmer 1983 Catalog Supplement p. B18.
Murray–Baumgartner Surgical Instrument Co. Catalog Dec. 26, 1934 p. 90.
Ohio Chemical advertisement in Journal of Bone and Joint Surgery vol. 45–A #7, Oct. 1963, p. 70.
Photograph of a Zimmer, Luque passing apparatus (date unknown).
Photograph of a Zimmer, Luque twisting apparatus (date unknown).

*Primary Examiner*—Stephen C. Pellegrino
*Assistant Examiner*—Scott B. Markow
*Attorney, Agent, or Firm*—Polster, Lieder, Woodruff & Lucchesi

[57] ABSTRACT

A single surgical instrument to both pass a wire under a bone and twist the ends of the wire together is comprised of a hooked member mounted to a handle assembly. The hooked member has a notch to feed a wire as the hooked member is pulled about the bone. The handle assembly incorporates a crank comprised of two handles rotatably mounted to a grip to thereafter quickly and tightly twist the wires about the bone with the same instrument.

14 Claims, 2 Drawing Sheets

5,501,688

SURGICAL DEVICE FOR MANIPULATING WIRE

BACKGROUND AND SUMMARY OF THE INVENTION

In the hands of a skilled surgeon, surgical instruments may be used to repair or replace broken or damaged Joints and limbs. Typically, these instruments are specifically designed for particular surgical tasks to improve the quality of the result, as well as to make the surgeon's job easier and faster. These latter two attributes produce hidden advantages. Making the surgeon's job easier reduces the surgeon's fatigue thereby conserving the surgeon's strength and alertness to ensure optimum performance throughout the entirety of lengthy surgeries. Saving time is of importance in surgical endeavors because risk to the patient is reduced by shortening the surgery.

One of the tasks encountered by surgeons is temporarily fastening bones together with wire. Primarily, this task arises in two settings, one being a bone fracture wherein the fragments may be temporarily joined by looping a wire around the fragments and twisting the ends of the wire about one another thereby tightening the loop to fasten the fragments in place. The other setting occurs during implant surgery wherein the bones need reinforcement to prevent them from splintering during the insertion of the implants. This is accomplished in much the same way as when fastening the fragments; the wire is looped around the bone and drawn tight.

The ends of the wires are normally preformed into loops which can be hooked with the instruments to aid in manipulation. In any one operation, numerous wires may be used to securely fasten the bones and distribute the reinforcement over a larger area. Because so many wires must be so tightly wound, the task can become fatiguing. In addition, as each wire must be manipulated around the bone, the end of the wire is hidden from sight thereby increasing the tedium associated with the task.

Prior to the present invention, passing the wire under the bone and twisting the ends required at least two instruments. The first prior art instrument was shaped something like a bent crochet hook. The end of this instrument was inserted underneath and around the bone, one of the looped ends of the wire was placed in the notch near the tip of the hook and the instrument was withdrawn to pull the wire underneath the bone. Then, a second instrument having a hook and an offset rotating handle was used to tightly twist the wires by placing the looped ends of the wire over the hook and orbiting the handle about the hook to cause the ends of the wire to wrap around one another to form a wire twist. When the desired tightness was achieved, the hook was extracted from the wire loop ends and the process was repeated as necessary. Thus, two prior art instruments were required to perform the tasks.

In order to solve these and other problems in the prior art, the inventor has succeeded in designing and developing a single surgical instrument to both pass the wire under the bone and twist its ends. The instrument has a handle assembly mounted on a rod-like axle member with a C-shaped hook at the end opposite the handle assembly. The hook is bent so that it lies in a plane substantially perpendicular to the handle assembly for ergonomic reasons. Thus, when the user holds the handle, the hook is more visible, and the user's hand is comfortably positioned to apply relatively large loads to the hook during insertion and extraction.

Unlike the prior art instrument, the new surgical instrument may be inserted and extracted by simply twisting the forearm. The prior art instrument required that the surgeon's hand move in a large arc about the patient's bone, a movement requiring greater effort and dexterity. Thus, the surgeon inserts the hook around the bone, places a looped end of the wire in a notch near the end of the hook and extracts the hook thereby pulling the wire around the bone. After the wire is pulled through, both ends of the wire are slipped around the hook and twisted by using the handle assembly. The handle assembly incorporates a crank with two handles separated by a grip so that the hook can be operated with two hands to quickly and tightly twist the wires about the bone. Unlike the prior art instrument, the hook of the new surgical instrument may easily be turned without swinging the wire ends significantly from side to side. Thus, lower cyclic loads are imparted on the bone and wire. The configuration of the handle assembly also allows the surgeon to apply tension to the wire as it is twisted so as to ensure that the wire is tightly twisted around the bone.

While the principal advantages and features of the present invention have been briefly described above, a greater understanding of the novel and unique features of the invention may be obtained by referring to the drawings and Detailed Description of the Preferred Embodiment which follow.

DETAILED DESCRIPTION OF THE PREFERRED EMBODIMENT

Figures 1, 2, 3:
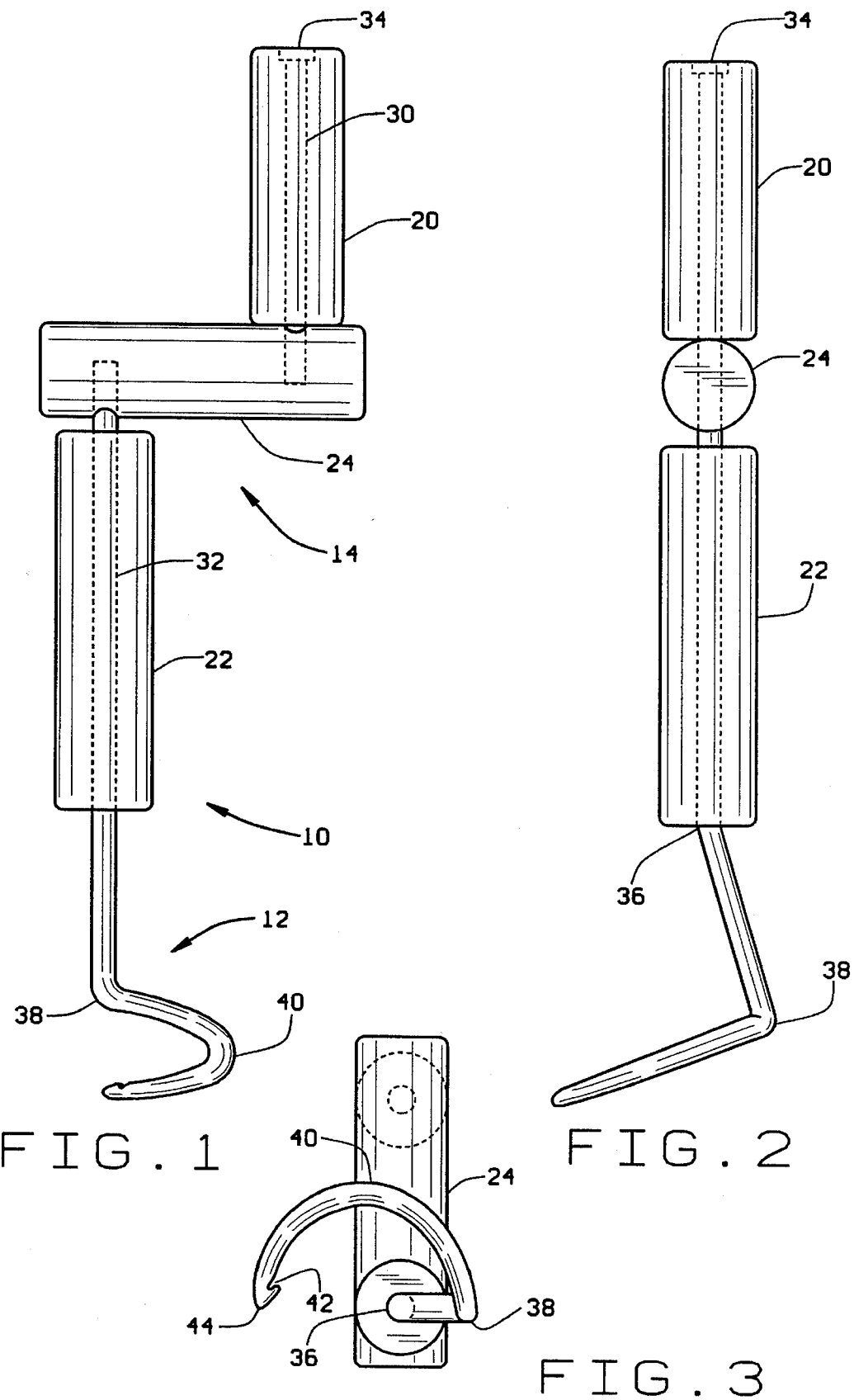
FIG. 1 is a front elevation view of the surgical instrument of the present invention.
FIG. 2 is a right side elevation view of the surgical instrument.
FIG. 3 is a bottom plan view of the surgical instrument showing the hook and notch geometry
Figure 4:
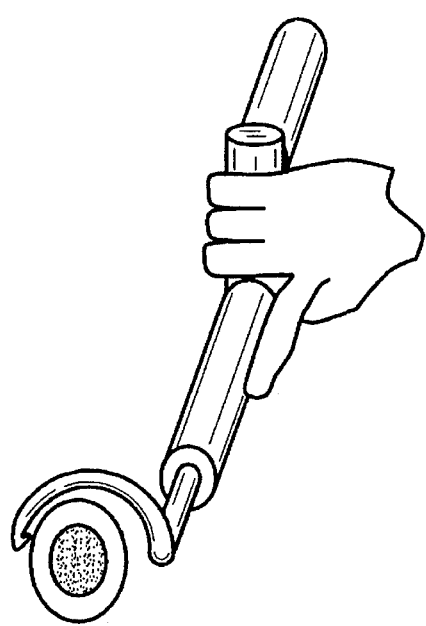
FIG. 4 is a diagram showing the steps of providing an instrument having a hook with a notch and a crank integrally joined with the hook, and of guiding the hook to partially surround the bone.
Figure 5:
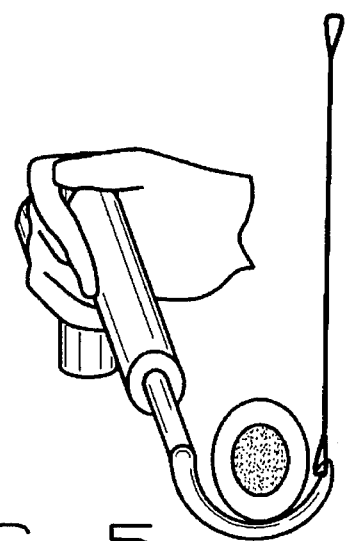
FIG. 5 is a diagram showing the step of attaching one looped end of the wire to the notch.
Figure 6:
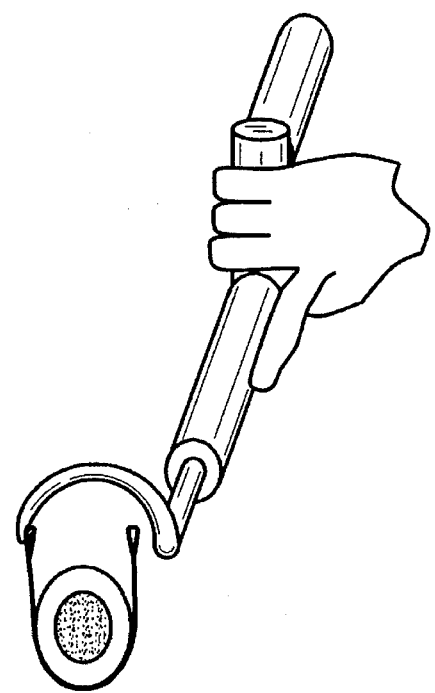
FIG. 6 is a diagram showing the step of withdrawing the hook from around the bone to thereby encircle the bone with the wire.
Figure 8:
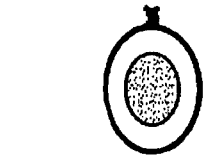
FIG. 8 is a diagram showing the wire tightened and secured to the bone.
Figure 7:
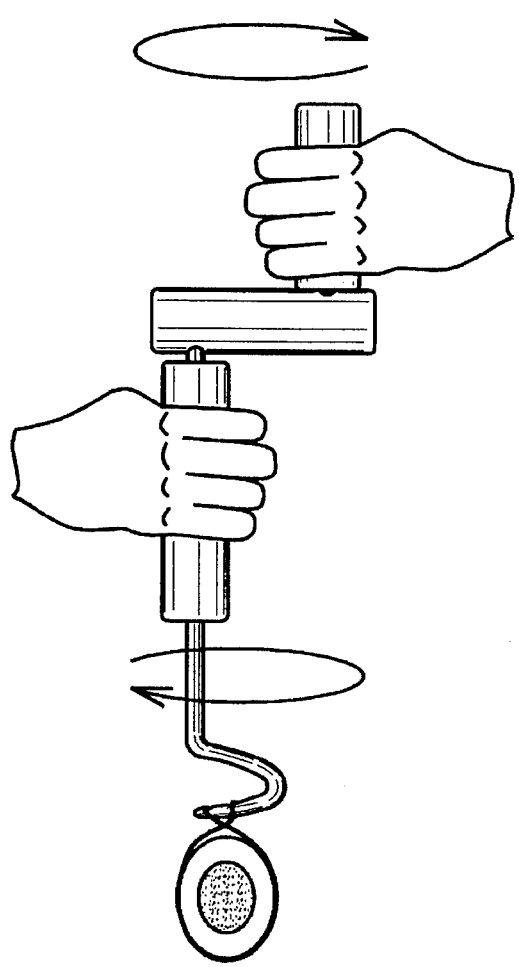
FIG. 7 is a diagram showing the steps of slipping the other looped end of said wire about said hook, and twisting said hook by turning the crank to rotate the hook and thereby tighten said wire about said bone and secure it thereto.

As shown in FIG. 1, the surgical instrument 10 is generally comprised of a hooked member 12 and a handle assembly 14. The handle assembly 14 is comprised of upper and lower handles 20, 22 as mounted to grip 24. Each of these handles and grip is approximately 1" to 2" in diameter so as to comfortably fit within the hand of the surgeon. The lower handle 22 is approximately 4" long so that the full width of the surgeon's hand may be accommodated. This provides adequate clearance between the grip and the patient when the instrument is "cranked" to twist the wire ends together, as explained below. The upper handle 20 is approximately 3" long and the grip 24 is approximately 3½"

long. Both the upper and lower handles 20, 22 freely spin so that the instrument may be cranked without tugging at the surgeon's glove. Upper handle 20 is mounted by rod 30 to grip 24, with head 34 retaining upper handle 20 in place while permitting its free rotation. Lower handle 22 is mounted to grip 24 by extension 32 of hooked member.

A bend 36 of approximately 15° at a point approximately 4½" below the grip 24 retains the lower handle 22 in position on extension 32. This bend 36 angles the hooked member 12 with respect to the handle assembly 14 so that as the hooked member 12 encircles the bone being worked on, the handle assembly 14 is thereby angled away from the bone to provide clearance for the surgeon's hands. Approximately 2" below the first bend 36 is a second bend 38 which is approximately 90°. This second bend 38 permits the surgeon to slide the hook 40 around a bone by merely twisting his wrist instead of orbiting his entire hand in a large arc as with the prior art device. The second bend 38 also assures that the wire ends are centered in the hook 40 as they are twisted together by turning the handle assembly.

As shown in FIG. 3, a notch 42 is formed near the distal end 44 of the hook 40. The notch 42 is angled up and away from the distal end 44 so that the wire is better retained as the hook 40 is retracted from around the bone. In addition, the notch 42 faces the bone so that it is less likely to catch on surrounding ligaments and other tissue as it is rotated about the bone. The hook 40 is tapered towards the distal end 44 along its length to make the wire loops easier to remove from the hook. So that the hook may easily circumscribe bones, the diameter along the hook centerline is approximately 2¼" and the distal end 44 of the hook 40 is beveled.

In the preferred embodiment, the hooked member 12, extension 32, rod 30, and grip 24 are made of 17-4 PH hardened stainless steel, and the handles are made of polyethylene. This combination inhibits corrosion and permits instrument sterilization by autoclave. The surgical instrument is intended for use with cobalt-chromium, titanium, or stainless steel wires or wires made of any other material. Typically, these wires are on the order of 0.032" in diameter.

Although different surgeons might develop a different technique, the hook 40 is generally configured as shown in FIG. 3 such that the grip 24 is held in the right hand during use. The hook is oriented relative to the grip such that when the surgeon grasps the grip in his right hand with the palm of the right hand facing to the right, the distal end 44 of the hook is pointing downward, thereby positioned for easy insertion to the right or behind a bone, depending upon the patient's orientation. As the hand is twisted in the clockwise direction, the hook is forced around the bone until the distal end is exposed from the left side or in front of the bone. The looped end of a wire can be inserted in the exposed notch. To withdraw the hook, the twisting motion is reversed and the wire is pulled around the bone in the process. Once the wire is around the bone, the hook is slipped through the second looped end of the wire and the first looped end allowed to slide out of the notch 42 such that the loops are close together approximately halfway between the distal end 44 and the lower bend 38. This location is best because the wires are nearly in line with the lower handle 22 to reduce the orbiting about the lower handle as the hook 40 is turned and so the loops are at the lowest point in the hook to aid in their retention. To twist the wire, the surgeon grasps the lower handle 22 in his left hand and cranks the upper handle 20 about the lower handle using his right hand. When the desired tightness is achieved, the surgeon simply withdraws the tapered hook from the wire loops. The resulting loop in the wire may be left momentarily until all the necessary wires are secured around the bone by repeating the procedure described above. Then the tapered hook can be reinserted as necessary into the wire loops to further tighten the twisted wires and thus ensure the correct tension in all the wires.

This technique, as described, is perhaps best suited for a right-handed surgeon. The present invention may be readily adapted to better suit a left-handed surgeon by being constructed in a mirror image. This would enable a left-handed surgeon to use the instrument with principally his left hand, in a pronating motion, as described above for a right-handed surgeon.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A surgical instrument for encircling and twisting a wire around a bone comprising:

a hook for encircling a portion of the bone and pulling the wire closely therearound to thereby at least partially encircle said bone, the hook having a notch for securing one of said wire ends; and a crank for rapidly twisting the ends of said wire together to thereby tightly draw the wire about the bone, said crank being joined to said hook.

2. The surgical instrument of claim 1 wherein the hook is oriented with respect to said crank so that said hook may be moved around the circumference of a generally cylindrical bone by the twisting of a surgeon's wrist when said crank is held in a surgeon's hand.

3. The surgical instrument of claim 2 wherein the crank includes a grip, said hook being joined to said grip by a member which has at least a portion substantially perpendicular to a plane defined by said hook.

4. The surgical instrument of claim 3 wherein the crank includes a pair of offset handles, said handles being rotatably mounted to said grip at opposite ends thereof.

5. The surgical instrument of claim 4 wherein the hook is tapered towards its distal end.

6. The surgical instrument of claim 5 wherein said hook distal end is beveled.

7. The surgical instrument of claim 4 wherein said portion of the member is angled with respect to at least one of the pair of handles.

8. The surgical instrument of claim 7 wherein said member portion and said at least one handle are angled by an angle of approximately 15°.

9. A surgical instrument for fastening a bone with a wire by circumscribing the bone with the wire and twisting ends of the wire together, said instrument comprising:

a hook configured to surround at least a portion of the bone for circumscribing the wire around the bone; and a crank for tightly twisting the wire ends together, the crank being joined with the hook.

10. The surgical instrument of claim 9 wherein the hook has a notch for securing an end of said wire.

11. The surgical instrument of claim 10 wherein said crank further comprises a grip fixed in position with respect to said hook, said hook being oriented with respect to said grip so that the notch may be guided around the perimeter of the bone by rotation of the grip.

12. The surgical instrument of claim 11 wherein the crank includes a pair of handles, said handles being spaced by and rotatively mounted to said grip.

13. The surgical instrument of claim 10 wherein the hook is tapered to the end.

14. A method of using a single instrument to reinforce a bone with a wire having looped ends, comprising:

providing a single instrument having a hook with a notch, the instrument including a crank integrally joined with the hook;

guiding the hook to partially surround the bone;

attaching one looped end of the wire to the notch;

withdrawing the hook from around the bone to thereby encircle the bone with the wire;

slipping the other looped end of said wire about said hook; and twisting said hook by turning the crank to rotate the hook and thereby tighten said wire about said bone and secure it thereto.

* * * * *